United States Patent [19]

Toy et al.

[11] 3,976,690

[45] Aug. 24, 1976

[54] PROCESS FOR PREPARING ALKANE BIS-DIHALOPHOSPHINES

[75] Inventors: Arthur D. F. Toy, Stamford, Conn.; Eugene H. Uhing, Pleasantville, N.Y.

[73] Assignee: Stauffer Chemical Company, Westport, Conn.

[22] Filed: Sept. 15, 1975

[21] Appl. No.: 613,683

[52] U.S. Cl............................. 260/543 P; 260/2 R; 526/57; 526/193; 526/319; 526/346
[51] Int. Cl.$^2$........................................... C07F 9/52
[58] Field of Search.............. 260/543 P, 2 R, 80 PS

[56] References Cited
UNITED STATES PATENTS

| | | | |
|---|---|---|---|
| 2,685,602 | 8/1954 | Woodstock et al. | 260/543 P |
| 2,852,565 | 9/1958 | Noyaki | 260/543 P |
| 3,206,508 | 9/1965 | Vilcsek et al. | 260/543 P |
| 3,397,122 | 8/1968 | Sennewald et al. | 260/543 P |

*Primary Examiner*—Norman Morgenstern
*Attorney, Agent, or Firm*—Paul J. Juettner

[57] ABSTRACT

Alkane bis-dihalophosphines are prepared by reacting an olefin with a trivalent phosphorus compound having three halogens attached thereto, such as phosphorus trichloride, in the presence of elemental phosphorus under at least autogenous pressure at a temperature of from 150°C. to 350°C. The compounds obtained are useful as intermediates in preparing organophosphorus compounds which can be used as insecticides, fungicides, pharmaceuticals, flame retardant compounds, and in forming metal complexes which are catalyst activators.

11 Claims, No Drawings

PROCESS FOR PREPARING ALKANE BIS-DIHALOPHOSPHINES

The present invention relates to a new and improved process for the preparation of alkane bis-dihalophosphines.

BACKGROUND OF THE PRESENT INVENTION

Alkane bis-dichlorophosphines are known compounds (see: Zur Spaltung tertiärer Phosphine, K. Sommer, Zeitschrift für anorganische und allgemeine Chemie, Band 376, pp. 37–43, 1970). These compounds are prepared by reacting a 1,2 ethyl bis-diphenyl phosphine with phosphorus trichloride in the presence of an aluminum chloride catalyst for 5 hours at 280°C. in a heated autoclave as per the following reaction:

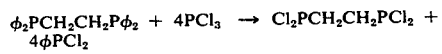

$\phi_2PCH_2CH_2P\phi_2 + 4PCl_3 \rightarrow Cl_2PCH_2CH_2PCl_2 + 4\phi PCl_2$

The yield is approximately 60%. However, this reaction requires a complex starting material which is difficult to prepare, and the 60% yield does not reflect losses in the preparation of the starting material. Also, this reaction requires high temperatures. Any reduction in the temperature would provide a definite cost and energy saving.

It is well known that phosphorus trihalide is an effective free radical scavenger. It is also known that phosphorus trihalide will react with olefins or ethylenically unsaturated compounds, generally in the presence of a catalyst to form monophosphine compounds (see: Radiation-induced Synthesis of Organophosphorus compounds, II. Products of Radiation-induced Synthesis from Mixtures of Olefins and Phosphorus trichloride, E. I. Babkina and I. V. Vereshchinskir, L. Ya., Zhurnal Obshchei Khimii, Vol. 41, No. 6, pp. 1248–1253, June, 1971; The Phosphorus Trichloride-Oxygen-Olefin Reaction: Scope and Mechanism, C. B. C. Boyce, S. B. Webb & L. Phillips, Journal Chemical Society, 1974, pp. 1650–1658; Radiation Induced Synthesis of Organophosphorus Compounds, Products of Radiation-induced Synthesis from Mixture of Hydrocarbons and Phosphorus Trichloride, E. I. Babkina and I. V. Vereshchinskii, Zhurnal Obshchei Khimii, Vol. 41, No. 8, pp. 1772–1776, August, 1968; A New Method of Preparation for Alkenylphosphonous Dichlorides and Alkenylthiophosphonic Dichlorides, Walsh, Beck and Woodstock, Journal of the American Chemical Society, 77, 929 (1955) (elemental phosphorus and iodine are used in a reaction with PCl₅ and an olefin to produce alkenyl phosphonous dichlorides); Photochemical Initiation of Radical-Chain Addition of Phosphorus Trichloride to Olefins, J. R. Little and P. F. Hartman, Journal of the American Chemical Society, 88, pp. 96 – 100, January 5, 1966; Addition of Phosphorus Trihalides to Olefins, B. Fontal and H. Goldwhite, Journal of Organic Chemistry, 31, pp. 3804–3806 (1966); C. Walling and M. S. Perason, Topics in Phosphorus Chemistry, Vol. 3, p. 11 E. J. Griffith and M. Grayson, Editors, Interscience, N.Y., 1966; New Reaction for the Production of Beta-chloroalkyldichlorophosphines from Olefins According to an Ionic Mechanism, A. I. Titov, M. V. Sizova, and P. O. Gitel, Doklady Akademii Nauk, S.S.S.R., Vol. 159, No. 2, pp. 385-388, November, 1964; U.S. Pat. Nos. 2,489,091, 2,510,699, 2,671,077, 2,671,078, 2,671,079, 2,671,080; Preparation of Long-chain Alkenylphosphonates, Nitta, Okamoto & Sakural, Yukagaku, 1969 18(10), 747–750 (Japan); Mechanism of Radical Chain Addition Reaction Termination for Phosphorus Trichloride Addition to Olefins, Shostenko, Zagoreta, Dadonov, Greish, Tr. Mesh Khim Tekhmd Inst., 1969, No. 62 100–103). All of these references basically relate to the reaction of an olefin with PCl₃ to form a RPCl₂ compound. Dihalophosphines are not contemplated nor formed by these reactions.

Applicants' co-pending application, Ser. No. 151,955, filed June 10, 1971, teaches that bis-phosphonic and phosphinic halides and their sulfur analogs can be prepared by reacting an olefin such as ethylene, propylene and butylene with a trivalent phosphorus comound in the presence of $P_4O_{10}$ or $P_4S_{10}$ (the latter for the sulfur analogs) under at least autogenous pressure at a temperature of from 200°C. to 450°C. The compounds prepared by this method are pentavalent phosphorus compounds. Trivalent alkane bis-dihalophosphines cannot be prepared by this method.

It is also known that alkyl- or arylphosphonous dichlorides can be prepared from an alkyl or aryl halide, phosphorus trichloride and phosphorus at elevated temperatures in an autoclave at autogenous pressure (A Direct Synthesis of Alkyl (or Aryl) Dichloro- and Dibromophosphines, N. K. Bliznyuk, Z. N. Kvasha & A. F. Kolomiets, Zhurnal Obshchei Khimii, Vol. 37, No. 4, pp. 890–892, April, 1967). This method, however, cannot be used for the preparation of the alkane -bis-dihalophosphines.

THE INVENTION

In accordance with the present invention there is provided a new method for preparing alkane bis-dihalophosphines of the formula:

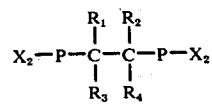

$$X_2-P-\underset{\underset{R_3}{|}}{\overset{\overset{R_1}{|}}{C}}-\underset{\underset{R_4}{|}}{\overset{\overset{R_2}{|}}{C}}-P-X_2 \qquad \text{I}$$

wherein X is chlorine or bromine and the groups $R_1$, $R_2$, $R_3$ and $R_4$ are independently selected from a group consisting of hydrogen and lower alkyl of from 1 to 10 carbon atoms which method comprises reacting a trivalent phosphorus compound of the formula:

$$PX_3 \qquad \text{II}$$

with an olefin of the formula:

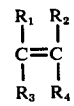

$$\underset{\underset{R_3}{|}\;\underset{R_4}{|}}{\overset{\overset{R_1}{|}\;\overset{R_2}{|}}{C=C}} \qquad \text{III}$$

in the presence of elemental phosphorus. The reaction is conducted at a temperature of from about 150°C. to about 350°C. under at least autogenous pressure. The following represents the theoretical stoichiometry of the reaction:

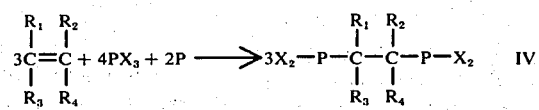

The process of the present invention generally requires no separate catalyst in order to effect reaction. However, it has also been found that, in reactions using long chain or complex olefins, a catalyst can be effectively used to raise yields. A catalyst can also be used to reduce the operating temperature of the reaction without affecting overall yields. Useful catalysts can be illustrated by iodine, bromine and compounds which carry the bromine or iodine moiety such as alkyl bromides and alkyl iodides, the latter being broadly illustrated by $C_1$ and generally up to $C_{10}$ alkyl iodides and bromides and specifically illustrated by ethyl iodide. Catalysts are generally used in an amount of from about 0.1% to 1% by weight, based on the weight of the charged olefin.

The preferred trivalent phosphorus compound is phosphorus trichloride and the preferred olefin is ethylene.

Some of the products of the present invention are known. The products of the present invention have utility as chemical intermediates particularly in the preparation of organophosphorus compounds which can be useful as insecticides, fungicides, pharmaceuticals and other organo phosphorus compounds such as organo phosphorus flame retardants. In addition, metal complexing agents which are useful as catalyst activators can be prepared from compounds having a $PCH_2CH_2P$ central moiety in the molecule (see: Some Recent Studies on Poly(tertiary) Phosphines and Their Metal Complexes, Bruce King, Accounts of Chemical Research, 5, 177 (1972)).

In formula No. II, $PX_3$, X is a halogen of chlorine or bromine. Preferably X is chlorine. The preferred reactant is phosphorus trichloride. The preferred group of compounds prepared by the method of the present invention are alkane bis-dichlorophosphines.

The olefins used in the method of the present invention are illustrated by the formula:

wherein $R_1$, $R_2$, $R_3$ and $R_4$ are independently selected from the group consisting of hydrogen and lower alkyl of from 1 to 10 carbon atoms. Some of the olefins which can be used are illustrated by ethylene, propylene, 1-butene, cis or trans 2-butene, isobutene, and 1-octene. Preferably, the olefin is selected from the group consisting of ethylene, propylene and 1-butene. More preferably, the olefin is ethylene.

It has been found that it is not necessary that the olefin be an alpha olefin. However, it has been found that alpha olefins give higher yields and are preferred for that reason.

The reaction of the present invention is conducted in the presence of elemental phosphorus. The elemental phosphorus can be used in any of its common elemental forms including yellow (or white) or red. Preferably, the yellow phosphorus form is used.

Stoichiometrically, the reaction for preparing compounds in accordance with the method of the present invention requires a ratio of 3 moles of olefin to 4 moles of the trivalent phosphorus compound to 2 gram atoms of the elemental phosphorus. Stoichiometrically, 3 moles of product should be obtained using the amounts given hereinbefore. Applicants do not intend to be limited to the stoichiometric ratio of materials and amounts within the ranges of 2 to 4 moles of olefin to 4 to 10 moles of trivalent phosphorus compound of 1 to 3 gram atoms of phosphorus can be used. It is preferred that the trivalent phosphorus compound be used in excess. Yields as high as 80% of the theoretical when using excess $PX_3$ can be obtained using the method of the present invention. Percent yield is generally calculated on the amount of olefin charged or on the elemental phosphorus charged based on equation IV shown on page 5.

The process of the present invention is carried out at elevated temperatures and at least under autogenous pressure. Temperatures of between about 150°C. and about 350°C. can be used though temperatures of from about 200°C. to about 300°C. are generally employed. It is not necessary that any one single reaction temperature be used. The temperature can be staged such that multiple successive reaction temperatures are used, the temperature falling within the range of 150–350°C. The method of the present invention may be conveniently effected by introducing the individual reactants into a reaction zone capable of withstanding elevated temperature and pressure, such as a metal bomb, autoclave or other pressure vessel, and carrying out the reaction under at least the autogenous pressure developed by the reactants at the reaction temperature. Pressures of up to 200 atmospheres above the autogenous pressure can also be used but are less desirable due to the inconvenience of requiring a pressurization system.

The time of reaction may vary over relatively wide limits as between about 1 to about 20 hours but a preferable reaction time has been found to be between about 5 and 12 hours.

The pressure reaction equipment is preferably equipped with an agitation mechanism such as a rocker, vibrator, or stirrer for best results. The presence of water or oxygen in the system is to be avoided since $PX_3$ will react with water. An inert atmosphere such as nitrogen can be used.

The reaction can be carried out in continuous or in batchwise systems, as desired.

The reaction can be conducted in the presence of diluents which can be gaseous, liquids or solid at room temperature, Compositions such as carbon tetrafluoride, perfluoroethane, benzene, toluene, hexane, as well as other hydrocarbons such as: ethane, propane, and the like are useful as diluents.

It is particularly advantageous to utilize the trivalent phosphorus compound as a diluent, particularly when the olefin is ethylene or 1-butene to prevent formation of a polymer type product. It has been found that an excess of at least about 25% and preferably about 50% $PX_3$ substantially reduces the polymer formation. Any excess or unreacted $PX_3$ can be recycled to successive reactions.

The products of the method of the present invention are purified by conventional means such as fractional distillation, crystallization and extraction. The identification of the products can be achieved by conventional methods, such as elemental analysis, and gas chromatography for purity, and mass spectrometry, nuclear magnetic resonance (phosphorus) and infrared analysis for structure.

Illustrative of the compound which can be prepared by the method of the present invention are:
$Cl_2PCH_2CH_2PCl_2$
$Br_2PCH_2CH_2PBr_2$
$Cl_2PCH(CH_3)CH_2PCl_2$
$Cl_2PCH(CH_3)CH(CH_3)PCl_2$
$Cl_2PCH_2CH(CH_2CH_3)PCl_2$
$Cl_2PCH_2CH[(CH_2)_5CH_3]PCl_2$
$Cl_2PC(CH_3)_2CH_2PCl_2$ The products of the present invention are bis-dihalides of trivalent phosphorus and therefore can be subject to all the known reactions which such compounds undergo.

The present invention will be more fully illustrated in the examples which follow:

EXAMPLE 1

Preparation of $Cl_2PCH_2CH_2PCl_2$ Using 108% Excess $PCl_3$

In a 300 milliliter 316 stainless steel autoclave were placed the following reactants:
92 grams $PCl_3$ (0.66 mole — 108% excess)
5 grams yellow phosphorus (0.161 gram atoms)
6.8 grams ethylene (0.242 moles)

The autoclave was heated until the temperature reached 270°C. and held at that temperature for 8 hours. After cooling there was no pressure in the autoclave. The crude yield of product was 77 grams of an orange colored liquid as against the theoretical pour out yield of 103.8 grams. Some orange solid containing absorbed liquid remained in the autoclave. Gas chromatography analysis of the crude liquid showed 72.2% $PCl_3$ and 27.8% product as against the theoretical ratio of 46% $PCl_3$ and 54% product. The product was isolated by distillation. The boiling point of the product at 1 millimeter of mercury pressure was 70°–90°C. Yield of product was 22.7 grams or 40% of the theoretical yield. Gas chromatography analysis showed purity to be 90%. The weight of non-distillables was 8 grams.

Analysis: Calculated for $Cl_2PCH_2CH_2PCl_2$: P = 26.8, Cl = 60; Found: P = 27.7, Cl = 60.3.

The nuclear magnetic resonance (phosphorus) spectra were consistent for the structure $Cl_2PCH_2CH_2PCl_2$.

EXAMPLE 2

Preparation of $Cl_2PCH_2CH_2PCl_2$ Using 55% Excess $PCl_3$

The following weights of reactants were split equally and placed into two 300 cubic centimeter 316 stainless steel high pressure autoclaves:
274 grams $PCl_3$ (2 moles — 55% excess)
19.9 grams yellow phosphorus (0.642 gram atoms)
29.2 grams ethylene (1.04 moles)

The two autoclaves were heated at 175°C. for one hour and then heated at 195°C. for 12 hours. After cooling 290 grams of liquid were poured from the autoclaves. This was 90% of the weight charged into the autoclaves. The crude product was distilled to recover the unreacted $PCl_3$ and purify the product. 151 grams (1.1 moles) of unreacted $PCl_3$ was recovered. The yield of product was 111.0 grams having a boiling point of 55°–60°C. at a pressure of 0.05 millimeters of mercury.

The yield of 111.0 grams equals 0.478 moles of product based on the molecular weight of 232 for $Cl_2PCH_2CH_2PCl_2$. Theoretical yield based on yellow phosphorus is 223 grams. Actual yield based on phosphorus was 49.8%. Actual yield based on $PCl_3$ reacted was 71%. (1.1 moles $PCl_3$ recovered out of 2 moles added or 0.9 moles reacted.) Theoretically, 0.9 moles $PCl_3$ would give 0.675 moles. The weight of solid residue obtained from the autoclaves and the distillation apparatus was 30 grams.

EXAMPLE 3

Preparation of $Cl_2PCH_2CH_2PCl_2$ Using 29% Excess $PCl_3$

Using the same procedure as shown in Example 2 except charging the two autoclaves with the following weights:
274 grams $PCl_3$ (2.0 mole — 29% excess)
24 grams yellow phosphorus (0.775 gram atoms)
33.8 grams ethylene (1.21 moles)

The recovery of unreacted $PCl_3$ was 122.4 grams (0.895 moles). The yield of $Cl_2PCH_2CH_2PCl_2$ was 110 grams. Actual yield based on phosphorus was 41%. Actual yield based on $PCl_3$ reacted was 52.5%. The residue left in the autoclaves and distillation apparatus was 56 grams. This was a 26 gram increase of residue over that of Example 2. Therefore, the use of a larger excess $PCl_3$ as diluent as shown in Example 2 is desirable.

EXAMPLE 4

Preparation of $Cl_2PCH_2CH_2PCl_2$ Using 95% Excess $PCl_3$

The same procedure as used in Example 2 was repeated except that 95% excess $PCl_3$ was used. A single 300 milliliter stainless steel autoclave was charged with 145 grams of $PCl_3$ (1.06 moles), 8.4 grams yellow phosphorus (0.265 gram atoms) and 12 grams ethylene (0.427 moles). The excess $PCl_3$ is 95% based on starting P. The autoclave was heated at 160°C. for 2 hours and at 175°C. for 1 hour and then at 200°C. for 16 hours. There was a slow steady pressure drop during this time from 700 to 250 psig during the first 12 hours of heating after which it remained constant. The yield of $Cl_2PCH_2CH_2PCl_2$ was 51 grams (58% yield based on P).

EXAMPLE 5

Preparation of $Cl_2PCH_2-\overset{\underset{\displaystyle CH_3}{|}}{C}HPCl_2$ from Propylene In a 300 milliliter 316 stainless steel autoclave was placed the following
102 grams $PCl_3$ (0.75 mole or a 35% excess based on P)
8.6 grams yellow phosphorus (0.278 gram atoms)
16.8 grams propylene (0.4 moles)

The autoclave was heated at 200°C. for 10.5 hours. During this period the pressure dropped from 500 to 250 psig. The product was isolated by distillation. Yield was 25 grams of a product having a boiling point of 60°C. at 0.2 millimeters of mercury pressure.

EXAMPLE 6

Preparation of $Cl_2P-\underset{\underset{CH_3}{|}}{\overset{\overset{CH_3}{|}}{C}}-CH_2-PCl_2$ using isobutene removed by distillation and the products were isolated by distillation at high vacuum (0.1–0.05 mmHg). The crude products were purified by distillation to obtain initial yields. These products were further purified by distillation to obtain samples for nmr, elemental analysis, index of refraction and boiling points.

The experimental details and results are tabulated below:

TABLE I

| Example No. | Olefin | Amount grams Olefin | $PCl_3$ | Yellow Phosphorus | Reaction[1] Temperature °C. | Yield[2] % | $n_D^{25}$ | Boiling Point °C. at 0.1 mm Hg | Elemental Analysis %P | %Cl | $^{31}P$-nmr[3] δ (ppm) |
|---|---|---|---|---|---|---|---|---|---|---|---|
| 7 | Propylene | 22.8 | 165 | 11.2 | 200 | 66 | 1.5717 | 55 | 57.6 | 25.0 | –190.8; –190.6 |
| 8 | 1-butene | 36.0 | 163 | 13.5 | 225 | 34 | 1.5650 | 65 | 54.9 | 23.6 | –194.7; –191.3 |
| 9 | 1-butene | 39.0 | 171 | 14.4 | 200 | 47 | 1.5650 | 65 | 54.9 | 23.6 | –194.7; –191.3 |
| 10 | cis-2-butene | 37.5 | 165 | 14.0 | 250 | 12 | 1.5702 | 75 | 54.0 | 23.3 | –193.2 |
| 11 | cis-2-butene | 28.7 | 157 | 10.6 | 228 | 27 | 1.5702 | 75 | 54.0 | 23.3 | –193.2 |
| 12 | trans-2-butene | 34.8 | 165 | 14.0 | 250 | 12 | 1.5701 | 78 | 53.9 | 23.9 | –194.7; –193.3; –191.2 |
| 13 | trans-2-butene | 36.8 | 159 | 13.6 | 240 | 15 | 1.5701 | 78 | 53.9 | 23.9 | –194.7; –193.3; –191.2 |
| 14 | isobutene | 43.0 | 165 | 16.0 | 225 | 7 | 1.5706 | 70 | 52.5 | 24.0 | –191.6; –188.7 |
| 15 | isobutene | 28.0 | 152 | 10.2 | 205 | 14 | 1.5706 | 70 | 52.5 | 24.0 | –191.6; –188.7 |
| 16 | 1-octene | 62.3 | 167 | 11.5 | 200 | 16 | 1.5410 | 105 | — | — | –194.0 |
| 17 | 1-octene | 62.3 | 169 | 11.5 | 230 | 20 | 1.5410 | 105 | — | — | –194.0 |

[1]All runs for 12 hours;
[2]Yield based on crude distilled weight of product, and olefin charged.
[3]All shifts listed for the butene products are doublets or more complex spectra. All nmr data used $H_3PO_4$ as the reference.

A 300 milliliter stainless steel autoclave was charged with:
145 grams $PCl_3$ (1.06 moles)
9.0 grams yellow phosphorus (0.29 gram atoms)
22.5 grams isobutene (0.4 moles)

The autoclave was heated at 250°C. for 2 hours. The temperature was then elevated to 270°C. for 12 hours. No pressure drop was observed, the pressure remaining steady at 600 psig. The product was isolated by distillation. The yield was 6.0 grams. Vapor phase chromatography and hydrogen nuclear magnetic resonance confirmed existence of the product.

EXAMPLES 7 – 17

Various alkane bis-dihalophosphines were prepared using various olefins, i.e., propylene, 1-butene, cis and trans-2-butene, isobutene and 1-octene. All reactions were conducted in 300 milliliter 316 stainless steel autoclaves using a 50% excess of $PCl_3$. All reactions were run for 12 hours at the temperatures stated below. All charges contained about 1% iodine as catalyst based on the amount of yellow phosphorus charged. The butene reactions were charged by placing the yellow phosphorus, $PCl_3$ and iodine in a dry 300 milliliter autoclave. The autoclave was closed and cooled in a solid carbon dioxide acetone bath to a temperature of between –70°C. and –80°C. The autoclave was then evacuated to 15 millimeters mercury pressure and the olefin was added as a gas which condensed in the autoclave.

All autoclaves were placed in a rocking heating jacket and heated to the reaction temperature for a period of 12 hours. After the reaction period, each autoclave was vented and the crude product was placed in a vacuum distillation flask. The excess $PCl_3$ was

EXAMPLE 18

Preparation of $Cl_2PCH_2CH_2PCl_2$ Using no Excess $PCl_3$

In a 300 milliliter 316 stainless steel autoclave were placed the following reactants:
82 grams $PCl_3$ (0.599 moles — 0% excess)
13 grams yellow phosphorus (0.419 gram atoms)
15 grams ethylene (0.536 moles)
0.1 grams iodine The autoclave was heated at 205°C. for 12 hours after which the crude product was poured from the autoclave. The crude product contained 17.7 grams of an orange solid which was isolated by filtration. The liquid yield was 56 grams which was a mixture of unreacted $PCl_3$ and product ($Cl_2PCH_2CH_2PCl_2$).

The soluble product was isolated by evaporation of the liquid fraction. A thick syrup weighing 11 grams was obtained.

The orange solid was placed in 6% aqueous HCl and 30% $H_2O_2$ was added thereto slowly. After 35 milliliters of $H_2O_2$ had been added, no more heat was liberated. The reaction was stirred for 3 hours during which time the orange solid was bleached to a white product. The yield of white solid was 12 grams. This material does not burn when placed in a yellow bunsen burner flame.

EXAMPLE 19

Control: Reaction of Olefin and $PX_3$ with no Elemental Phosphorus

A. Ethylene and $PCl_3$, Iodine Catalyst

In a 316 stainless steel autoclave were placed 27 grams (0.96 moles) of ethylene, 140 grams (1.02 moles) of $PCl_3$ (ratio 1:1) and 0.1 grams of iodine as catalyst. The mixture was reacted for 12 hours at 200°C. Analysis of the products by $^{31}$P-nmr showed that 97% of the phosphorus was unreacted PCl$_3$.

A similar experiment run at 220°C. gave a 7% yield of 1,2 ethane bis-dichlorophosphine along with an almost equal weight of black powder.

B. Propylene, PCl$_3$ and Iodine Catalyst

In a 316 stainless steel autoclave were placed 45 grams (1.07 moles) of propylene, 135 (0.985 moles) of PCl$_3$ and 0.1 grams of iodine as catalyst. The mixture was reacted for 12 hours at 200°C. Analysis of the products by $^{31}$P-nmr showed that 98% of the phosphorus was unreacted PCl$_3$.

C. Isobutene, PCl$_3$ and Iodine Catalyst

In a 316 stainless steel autoclave were placed 47 grams (0.84 moles) of isobutene, 101.6 grams (0.74 moles) of PCl$_3$, and 1 gram of iodine. The mixture of reactants was reacted for 12 hours at 210°C. While 46% (0.39 moles) of the charged isobutene was consumed in the reaction, no identifiable level of bis-dihalophosphine type product was formed. The reaction formed 16.65 grams (0.18 moles) of tert-butyl chloride and 25.8 grams (0.1 moles) of butenephosphonous dichloride.

As is shown in Example 15 in a similar experiment using elemental phosphorus, a yield of 14% of crude distilled product based on olefin charged is obtained.

EXAMPLE 20

Preparation of Cl$_2$P(S)CH$_2$CH$_2$P(S)Cl$_2$

To Cl$_2$PCH$_2$CH$_2$PCl$_2$ is added sulfur at a ratio of two moles sulfur per mole of Cl$_2$PCH$_2$CH$_2$PCl$_2$ and aluminum chloride as catalyst. The reaction is conductive according to the procedure outlined in Zur Spaltung tertiärer Phosphine, K. Sommer, Zeitschrift für anorganische und allgemeine Chemie, Band 376, pp. 37–43, on page 40. Cl$_2$P(S)CH$_2$CH$_2$P(S)Cl$_2$ is prepared.

EXAMPLE 21

Use of Cl$_2$P(S)CH$_2$CH$_2$P(S)Cl$_2$ As a Flame Retardant for Polystyrene or Polymethyl Methacrylate Styrene was mixed with 15 weight percent of Cl$_2$P(S)CH$_2$CH$_2$P(S)Cl$_2$ and 0.5 weight percent benzoyl peroxide as catalyst. Sufficient amount of this mixture was placed in a ½ inch diameter test tube to make a rod approximately 2 inches long. The test tube was purged with nitrogen and sealed. The test tube was heated at 60°C. for 8 hours. The tube was cooled and then broken to provide a polystyrene rod of a diameter approximately ½ inch and a length of approximately 2 inches.

A similar polymethyl methacrylate rod was prepared using methyl methacrylate in place of styrene.

Both rods were tested for flammability by determining their limiting oxygen index (LOI) as compared to a blank of the same polymer having no flame retardant incorporated therein by means of ASTM test D-2863. This procedure is also described by Fenimore and Martin in the November, 1966, issue of Modern Plastics. In brief, the LOI directly relates flame retardancy to a measurement of the minimum percentage concentration of oxygen in an oxygen:nitrogen mixture which permits the sample to burn; the LOI being calculated as follows:

$$LOI = \frac{[O_2]}{[O_2] + [N_2]} \times 100$$

Thus, a higher LOI is indicative of a higher degree of flame retardancy.

The following results were achieved:

TABLE II

| Polymer | % Loading | LOI | BLANK |
|---|---|---|---|
| Polystyrene | 15% | 21.90 | 18.75* |
| Polymethyl methacrylate | 15% | 22.20 | 17.80 |

*This rod seemed to pop while in the oven during the polymerization stage.

Because the samples containing the compound Cl$_2$P(S)CH$_2$CH$_2$P(S)Cl$_2$ had higher LOI's than their respective blanks, the Cl$_2$P(S)CH$_2$CH$_2$P(S)Cl$_2$ increased the flame retardancy of both polymer samples.

The present invention is defined in the claims which follow.

What is claimed is:

1. A method for preparing compounds of the formula:

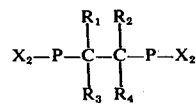

wherein X is chlorine or bromine, and R$_1$, R$_2$, R$_3$ and R$_4$ are independently selected from the group consisting of hydrogen, and alkyl of 1 to 10 carbon atoms which comprises; reacting under at least autogenous pressure, at a temperature of from about 150°C. to about 350°C. an ethylenically unsaturated compound of the formula:

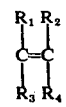

with a phosphorus compound of the formula:

in the presence of elemental phosphorus wherein R$_1$, R$_2$, R$_3$, R$_4$ and X being as defined hereinabove.

2. The method as recited in claim 1 wherein X is chlorine.

3. The method as recited in claim 1 wherein R$_1$, R$_2$, R$_3$, and R$_4$ are hydrogen.

4. The method as recited in claim 1 wherein at least 25% excess of PX$_3$ is used over that stoichiometric amount required to react the ethylenically unsaturated compound with PX$_3$ in the presence of elemental phosphorus.

5. The method as recited in claim 4 wherein the excess ranges between 50% and 125%.

6. The method as recited in claim 1 wherein said ethylenically unsaturated compound is selected from the group consisting of ethylene, propylene, 1-butene, cis-2-butene, trans-2-butene, isobutene, and 1-octene.

7. The method as recited in claim 1 which further includes a catalyst.

8. The method as recited in claim 7 wherein said catalyst is selected from the group consisting of iodine, bromine, alkyl bromides and alkyl iodides.

9. The method as recited in claim 1 wherein said temperature is from about 200°C. to about 300°C.

10. The method as recited in claim 4 which includes the further step of recycling unreacted $PX_3$ to the next reaction sequence.

11. The method as recited in claim 1 wherein multiple successive reaction temperatures are used.

* * * * *